United States Patent
Ouchi

Patent Number: 6,033,424
Date of Patent: Mar. 7, 2000

[54] TREATING INSTRUMENT FOR ENDOSCOPE

[75] Inventor: Teruo Ouchi, Saitama, Japan

[73] Assignee: Asahi Kogaku Kogyo Kabushiki Kaisha, Tokyo, Japan

[21] Appl. No.: 09/233,030

[22] Filed: Jan. 20, 1999

[30] Foreign Application Priority Data

Feb. 4, 1998 [JP] Japan .................................. 10-022474

[51] Int. Cl.[7] ........................... A61B 17/28; A61B 17/42
[52] U.S. Cl. ............................................. 606/205; 606/207
[58] Field of Search .................................. 606/205, 206, 606/207, 208, 209, 210, 51, 52; 600/152, 154

[56] References Cited

U.S. PATENT DOCUMENTS 5,609,599  3/1997  Levin .................................. 606/153
5,906,630  5/1999  Anderhub et al. .................. 606/205

FOREIGN PATENT DOCUMENTS 6114075    4/1994   Japan .
6-296619   10/1994  Japan .
8140985    6/1996   Japan .
8164141    6/1996   Japan .

Primary Examiner—Michael Buiz
Assistant Examiner—Vy Q. Bui
Attorney, Agent, or Firm—Greenblum & Bernstein, P.L.C.

[57] ABSTRACT

A treating instrument for an endoscopic treatment has a pair of treating members at the distal end of a sheath. The treating members are opened or closed in a beaklike manner by a control wire axially movably inserted in the sheath. A pair of links of different lengths are integrally connected to the treating members, respectively. A pair of intermediate links of different lengths are rotatably connected at one end thereof to the pair of links, respectively, and driven at the other end thereof by the control wire so as to move back and forth. The shorter intermediate link is connected to the longer link. The longer intermediate link is connected to the shorter link.

7 Claims, 5 Drawing Sheets

TREATING INSTRUMENT FOR ENDOSCOPE

BACKGROUND OF THE INVENTION

The present disclosure relates to subject matter contained in Japanese Patent Application No. 10-22474 (filed on Feb. 4, 1998), which is expressly incorporated herein by reference in its entirety.

1. Field of the Invention

The present invention relates to a treating instrument used through an instrument-inserting channel of an endoscope.

2. Description of the Prior Art

A treating instrument for an endoscopic treatment, such as a biopsy forceps used with an endoscope, has a pair of treating members provided at the distal end of a sheath that is removably inserted into an instrument-inserting channel of an endoscope. The pair of treating members are opened or closed in a beaklike manner by remote control conducted at the proximal end of the sheath.

Such endoscopic treating instruments include two different types: a bilaterally opening type in which both a pair of treating members are opened or closed in opposite directions through the same angle; and a unilaterally opening type in which only one of a pair of treating members is rotatable to perform an opening and closing action, the other being fixed.

The unilaterally opening type is clumsy and likely to cause a misoperation because only one treating member is rotatable when the treating instrument is used to hold the mucous membrane of an affected part between the pair of treating members. For this reason, the bilaterally opening type is widely used.

If an affected part on the mucous membrane surface in a body cavity lies just in front of a treating instrument projecting from the instrument-inserting channel of an endoscope, the above-described conventional bilaterally opening type of treating instrument can be effectively used. In such a case, the mucous membrane of the affected part can be readily held with the pair of treating members to perform a necessary endoscopic treatment.

However, when an affected part to be treated is situated where the pair of treating members of the endoscopic treating instrument can be aimed at it only in a diagonal direction (such cases are encountered quite often in actual practice), it is difficult to hold the mucous membrane of the affected part with the pair of treating members. Therefore, there are not a few cases where an endoscopic treatment cannot smoothly be performed.

SUMMARY OF THE INVENTION

An object of the present invention is to provide a treating instrument for an endoscopic treatment designed so that even when an affected part to be treated is situated to face in a diagonal direction with respect to the axis of the sheath, tissue of the affected part is readily held between a pair of treating members of the bilaterally opening type, thereby enabling an endoscopic treatment to be performed smoothly and safely.

Other objects and advantages of the present invention will become apparent from the following detailed description of an illustrated embodiment of the invention.

According to the present invention, there is provided a treating instrument for an endoscopic treatment in which a pair of treating members are provided at the distal end of a sheath so that the pair of treating members are opened or closed in a beaklike manner by a control wire axially movably inserted in the sheath. A pair of links of different lengths are integrally connected to the pair of treating members, respectively. A pair of intermediate links of different lengths are rotatably connected at one end thereof to the pair of links, respectively. The pair of intermediate links are driven at the other end thereof by the control wire so as to move back and forth. A shorter intermediate link of the pair of intermediate links is connected to a longer link of the pair of links, and a longer intermediate link of the pair of intermediate links is connected to a shorter link of the pair of links.

BRIEF DESCRIPTION OF THE DRAWINGS

The present invention may be more fully understood from the description of a preferred embodiment of the invention set forth below, together with the accompanying drawings, in which.

DESCRIPTION OF THE EMBODIMENT

An embodiment of the present invention will be described below with reference to the accompanying drawings.

Figure 1:
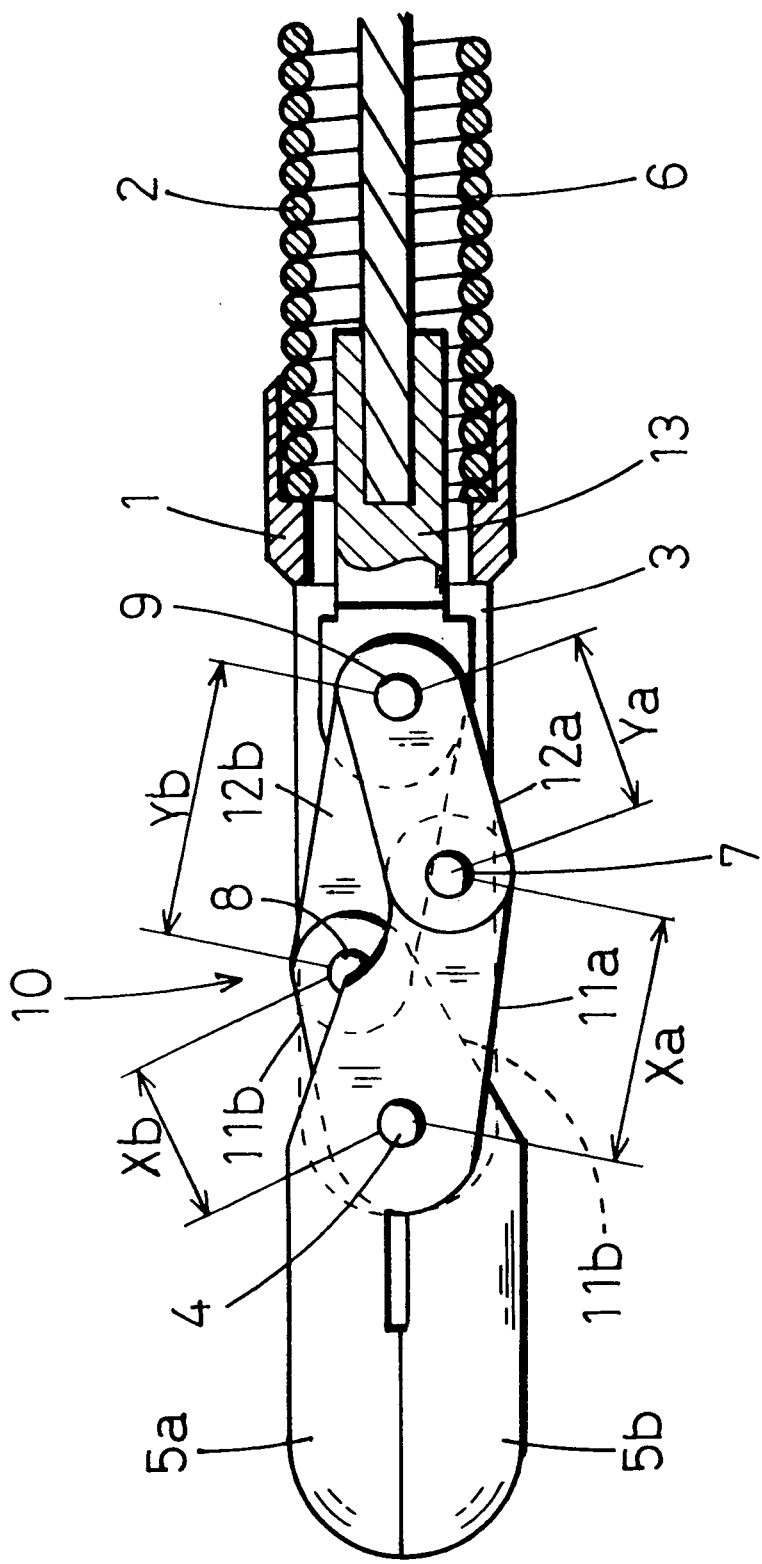
FIG. 1 is a sectional side view showing a distal end portion of a treating instrument for an endoscopic treatment according to an embodiment of the present invention in a state where a pair of treating members are closed.

FIG. 1 shows a distal end portion of a biopsy forceps for an endoscope to which the present invention is applied. A flexible sheath 2 is removably inserted into an instrument-inserting channel of an endoscope (not shown). The sheath 2 is formed from a coil pipe that is formed by close-winding a stainless steel wire, for example. A distal end block 1 is firmly connected to the distal end of the sheath 2. The distal end block 1 has a large slit 3 cut from the forward end thereof.

A pivot shaft 4 is mounted on the distal end block 1 in such a way as to cross the distal end portion of the slit 3. A pair of forceps cups (treating members) 5a and 5b for taking a piece of tissue for a biopsy specimen are each rotatably supported by the pivot shaft 4. As shown in FIG. 1, when the forceps cups 5a and 5b are closed, both the forceps cups 5a and 5b extend in the same direction as the axis of the sheath 2.

A link mechanism 10 for opening and closing the pair of forceps cups 5a and 5b is placed in the slit 3. The link mechanism 10 has four links 11a, 12a, 11b and 12b that are connected together so as to be rotatable relative to each other in the form of a pantograph.

Two forward links 11a and 11b in the link mechanism 10 are each integral and contiguous with the first forceps cup 5a or the second forceps cup 5b and rotatable about the pivot shaft 4.

Two intermediate links 12a and 12b are rotatably connected to the two links 11a and 11b by first and second connecting shafts 7 and 8, respectively. The rear ends of the two intermediate links 12a and 12b are rotatably connected to a driving rod 13 by a third connecting shaft 9.

A control wire 6 is axially movably inserted in the sheath 2. The distal end of the control wire 6 is firmly connected to the link mechanism 10. The control wire 6 is remote-controlled from the proximal end of the sheath 2 (the right-hand side as viewed in FIG. 1) to cause the driving rod 13 to move back and forth in the axial direction. This causes the link mechanism 10 to operate, thereby enabling the pair of forceps cups 5a and 5b to be opened or closed in a beaklike manner.

Of the four links 11a, 12a, 11b and 12b, which form the link mechanism 10, the link 11a connected to the first forceps cup 5a has a length (distance between the two support shafts) Xa longer than the length Xb of the link 11b connected to the second forceps cup 5b. That is, Xa>Xb.

The length Ya of the intermediate link 12a connected to the first link 11a is shorter than the length Yb of the intermediate link 12b connected to the second link 11b. That is, Ya<Yb. It should be noted that in this embodiment the lengths of the four links 11a, 12a, 11b and 12b are set at Xa+Ya=Xb+Yb. However, it is not always necessary to do so.

In the treating instrument according to this embodiment, which is arranged as stated above, when the link mechanism 10 is activated by moving the control wire 6 back and forth, the pair of forceps cups 5a and 5b are opened or closed simultaneously. At this time, the angle through which the second forceps cup 5b rotates is larger than the rotation angle of the first forceps cup 5a.

Figure 2:
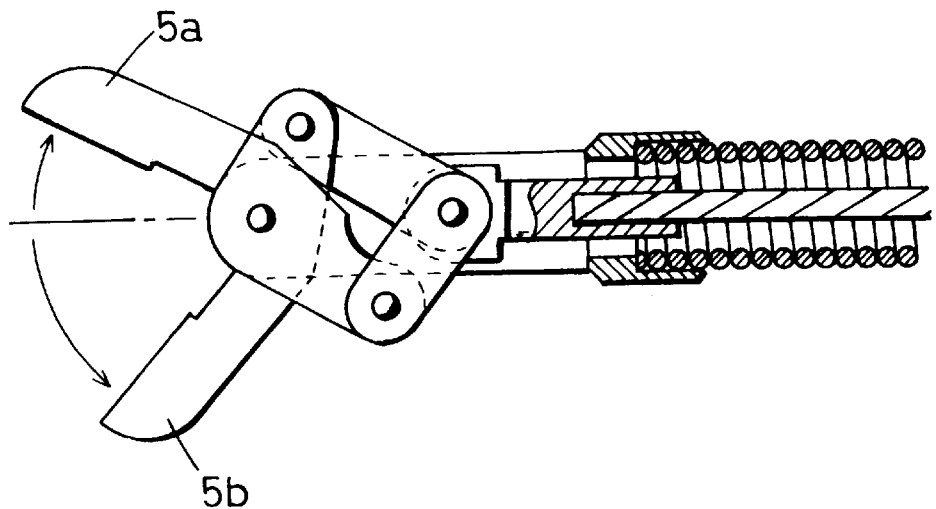
FIG. 2 is a sectional side view showing the distal end portion of the treating instrument according to the embodiment of the present invention in a state where the pair of treating members are being opened.
Figure 3:
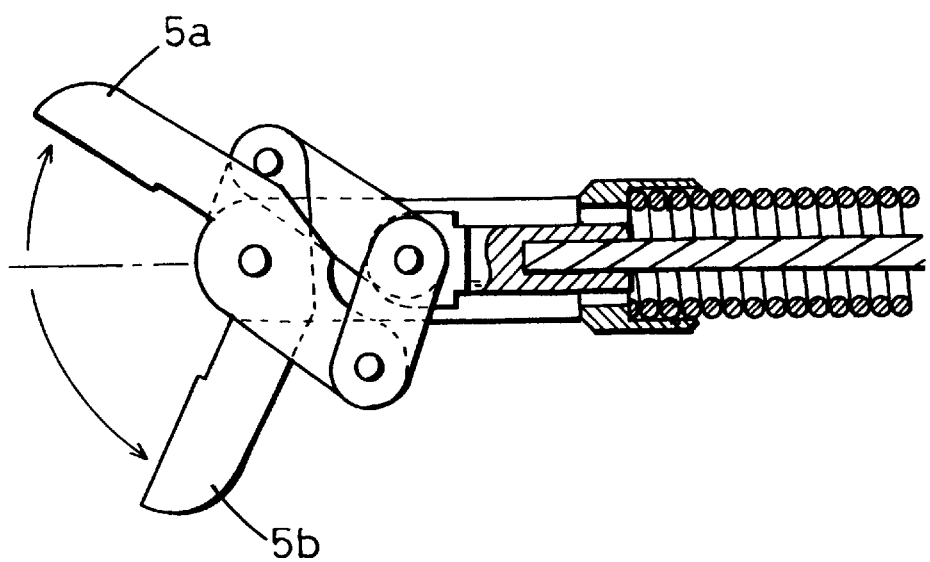
FIG. 3 is a sectional side view showing the distal end portion of the treating instrument according to the embodiment of the present invention in a state where the pair of treating members are being opened.

Accordingly, when the control wire 6 is pushed toward the distal end of the sheath 2, the forceps cups 5a and 5b open as shown sequentially in FIGS. 2 and 3. At this time, the second forceps cup 5b opens to a greater extent than the first forceps cup 5a.

Figure 4:
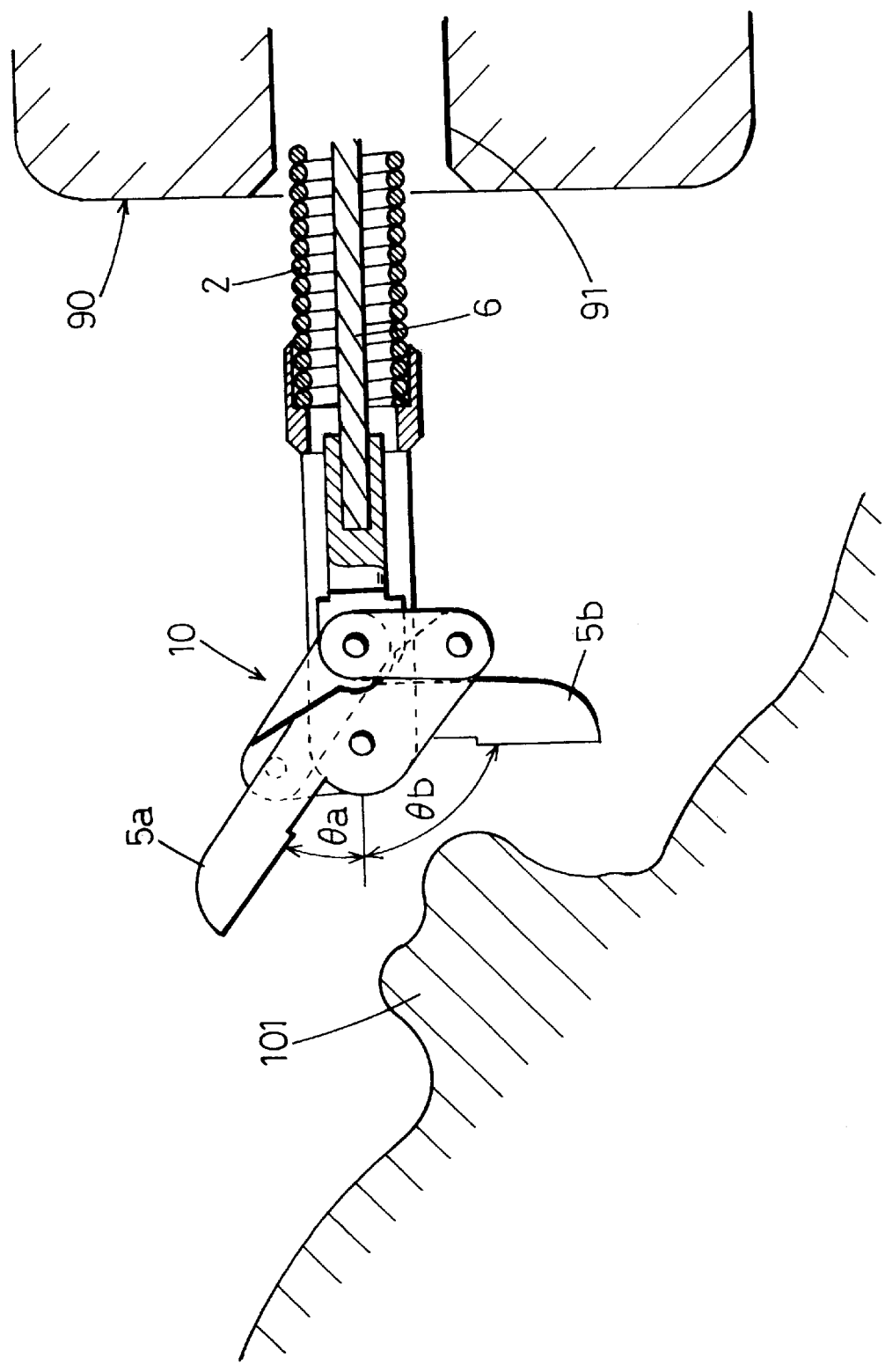
FIG. 4 is a sectional side view showing the distal end portion of the treating instrument according to the embodiment of the present invention in a state where the pair of treating members are open to the full.

FIG. 4 shows a state where the pair of forceps 5a and 5b projecting from the distal end of an instrument-inserting channel 91 of an endoscope 90 are open to the full. The opening angle θb of the second forceps cup 5b is larger than the opening angle θa of the first forceps cup 5a. That is, θa<θb.

It should be noted that, in this embodiment, θa=30°, and θb=90°. Accordingly, θa+θb=120°, and θb/θa=3.0.

However, the practical maximum opening angle (θa+θb) of the pair of forceps cups 5a and 5b is within the range of from 90° to 120°. θa and θb can be set in various combinations, including those shown below by way of example:

---
Example 1: θa = 30°, θb = 60° (θb/θa = 2.0)
Example 2: θa = 40°, θb = 60° (θb/θa = 1.5)
Example 3: θa = 22°, θb = 88° (θb/θa = 4.0)
---

In such settings, it is preferable from the viewpoint of practical use that the maximum opening angle ratio θb/θa of the forceps cups 5a and 5b should be within the range of from 1.5 to 4.0, more desirably from 2.0 to 3.0. It has been confirmed that when the maximum opening angle ratio θb/θa is within the above-described range, the treating instrument is easy to use. Therefore, the ratio between the lengths of the links 11a and 11b and the intermediate links 12a and 12b should be determined so as to satisfy the above-described condition.

Consequently, even in a case where, as shown in FIG. 4, an affected part 101 on the mucous membrane surface is situated on a slant surface tilted to a considerable extent with respect to the axis of the sheath 2, the forceps cups 5a and 5b can be opened so as to face in the direction in which the affected part 101 projects. Therefore, a piece of tissue of the affected part 101 can be readily cut for a biopsy specimen by closing the forceps cups 5a and 5b opened as stated above.

The treating instrument, which operates as described above, is easy to use because both the pair of forceps cups 5a and 5b are rotatable to perform an opening and closing action. That is, the treating instrument is of the bilaterally opening type. Accordingly, the opposing directions of the forceps cups 5a and 5b can be changed by rotating the sheath 2 about its own axis at the proximal end thereof. Therefore, the treating instrument can be readily aimed at the affected part 101 simply by rotating the sheath 2 about the axis thereof.

Figure 5:
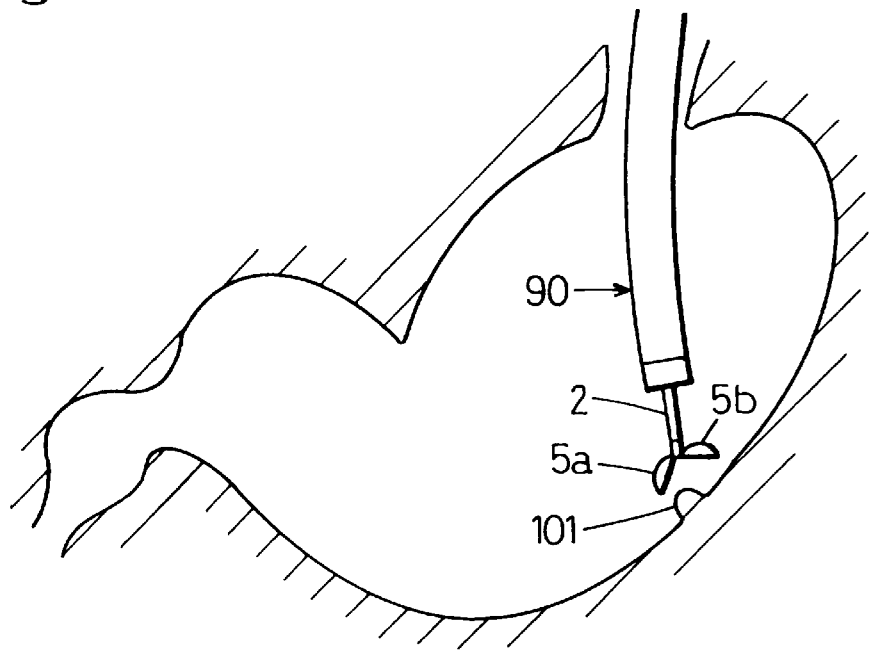
FIG. 5 is a schematic diagram showing the way in which the treating instrument according to the embodiment of the present invention is used in the stomach.
Figure 6:
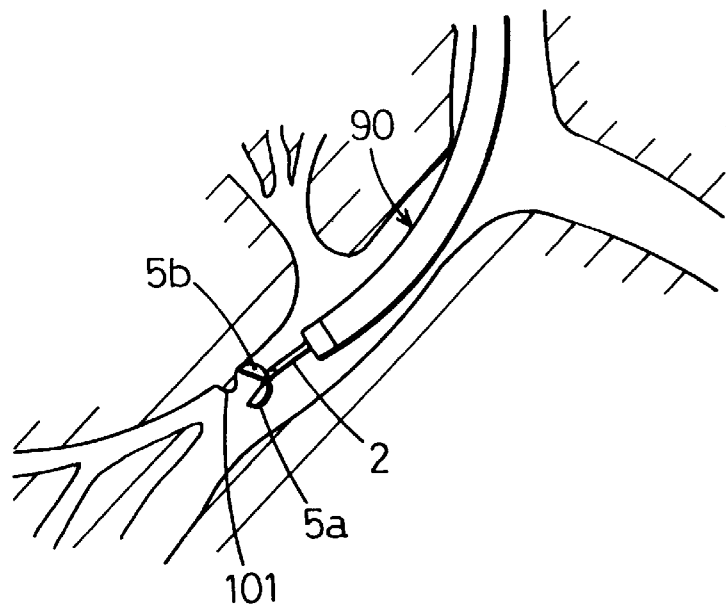
FIG. 6 is a schematic diagram showing the way in which the treating instrument according to the embodiment of the present invention is used in a bronchial tube.
Figure 7:
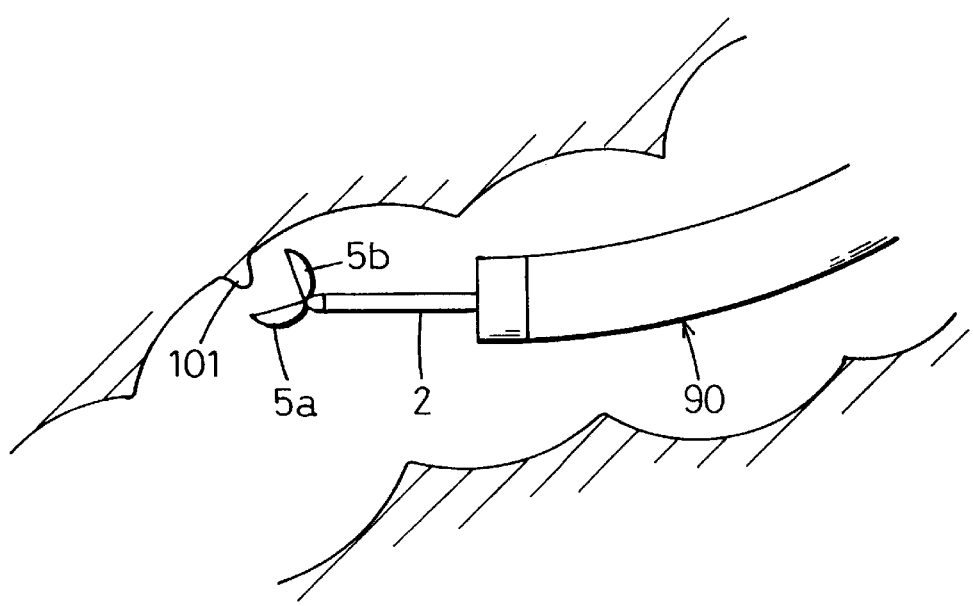
FIG. 7 is a schematic diagram showing the way in which the treating instrument according to the embodiment of the present invention is used in the intestines.

FIGS. 5, 6 and 7 show the ways in which the treating instrument according to the present invention is used in the stomach, a bronchial tube, and the intestines, respectively. In these parts of the body, the treating instrument can be readily aimed at the affected part 101 and smoothly operated to grasp it. Thus, the present invention provides a treating instrument favorably improved in the aiming and grasping capability.

It should be noted that the present invention is not necessarily limited to the biopsy forceps for an endoscope but can be applied to various other treating instruments used with an endoscope, for example, holding forceps.

According to the present invention, a longer link is connected to one of a pair of treating members of the bilaterally opening type that are provided at the distal end of a sheath, and a shorter link is connected to the other treating member. A shorter intermediate link is connected to the longer link, and a longer intermediate link is connected to the shorter link. Accordingly, the pair of treating members are opened or closed through different rotation angles. Therefore, even when an affected part to be treated is situated to face in a diagonal direction with respect to the axis of the sheath, the pair of treating members can be readily aimed at the affected part, and an endoscopic treatment can be performed smoothly and safely.

While the invention has been described by reference to a specific embodiment chosen for purposes of illustration, it should be apparent that numerous modifications could be made thereto by those skilled in the art without departing from the basic concept and scope of the invention.

What is claimed is:

1. A treating instrument for an endoscopic treatment in which a pair of treating members are provided at a distal end of a sheath so that said pair of treating members are opened or closed in a beaklike manner by a control wire axially movably inserted in said sheath, said treating instrument comprising:

a pair of links integrally connected to said pair of treating members, respectively, said pair of links having different lengths; and a pair of intermediate links rotatably connected at one end thereof to said pair of links, respectively, and driven at the other end thereof by said control wire so as to move back and forth, said pair of intermediate links having different lengths;

wherein a shorter intermediate link of said pair of intermediate links is connected to a longer link of said pair of links, and a longer intermediate link of said pair of intermediate links is connected to a shorter link of said pair of links.

2. A treating instrument according to claim 1, wherein a sum of the length of the longer link of said pair of links and the length of the shorter intermediate link of said pair of intermediate links is equal to a sum of the length of the shorter link and the length of the longer intermediate link.

3. A treating instrument according to claim 1, wherein when closed, both said pair of treating members extend in a same direction as an axis of said sheath.

4. A treating instrument according to claim 3, wherein a ratio of a maximum opening angle of one of said treating members to a maximum opening angle of the other is within a range of from 1.5 to 4.0.

5. A treating instrument according to claim 4, wherein the ratio of the maximum opening angle of one of said treating members to the maximum opening angle of the other is within a range of from 2.0 to 3.0.

6. A treating instrument according to claim 1, wherein a total opening angle of said pair of treating members is within a range of from 90° to 120°.

7. A treating instrument according to claim 1, wherein said pair of treating members are forceps cups for taking a piece of tissue for a biopsy specimen.

* * * * *